United States Patent [19]
Thakur et al.

[11] Patent Number: 5,827,308
[45] Date of Patent: Oct. 27, 1998

[54] TONGUE SCRAPING APPARATUS

[75] Inventors: Hemant K. Thakur, Lenexa, Kans.; Robin W. Ream, Independence, Mo.

[73] Assignee: Beyond 21st Century, Inc., Lenexa, Kans.

[21] Appl. No.: 810,604

[22] Filed: Feb. 28, 1997

[51] Int. Cl.$^6$ .............................. A61B 17/24; A61F 9/00
[52] U.S. Cl. ........................................ 606/161; 128/62 A
[58] Field of Search ................... 606/161; 128/62 A; 15/227, 210 A, 111; 132/84 A, 84 R

[56]     References Cited

U.S. PATENT DOCUMENTS 4,582,059  4/1986  Tiwari ............................... 132/84 A X

FOREIGN PATENT DOCUMENTS 0177011  12/1953  Denmark ............................. 606/161
2510391   2/1983  France ................................. 606/161

OTHER PUBLICATIONS

Oolitt tongue cleaner brochure, located on web page at www.breathcenter,com/scraping.htmi., dated Jan. 27, 1997.
The OraFresh Tongue Cleaner brochure, located on web page at www.webquill.com/%7Eorafresh, dated Jan. 27, 1997.

Primary Examiner—Michael Powell Buiz
Assistant Examiner—Nancy Mulcare
Attorney, Agent, or Firm—Shook, Hardy & Bacon L.L.P.

[57]     ABSTRACT

A tongue scraping apparatus is provided for use in cleaning the upper surface of a user's tongue. The apparatus includes a curved blade 10 presenting a parabolic plan shape and including a pair of proximal ends 14, and a pair of elongated handles 12, each including a distal end 24 connected to one of the proximal ends of the blade. The blade includes a relatively sharp lower edge 16, an opposed, relatively smooth upper edge 18, and opposed front and back faces 20, 22 extending between and connecting the lower and upper edges together. The handles 12 are each provided with a depending thumb press 28 for facilitating gripping of the apparatus, and the center of gravity of the apparatus is offset from the thumb presses in a direction toward the free ends 26 of the handles so that the apparatus rests on the free ends and thumb presses when placed on a horizontal support surface.

13 Claims, 1 Drawing Sheet

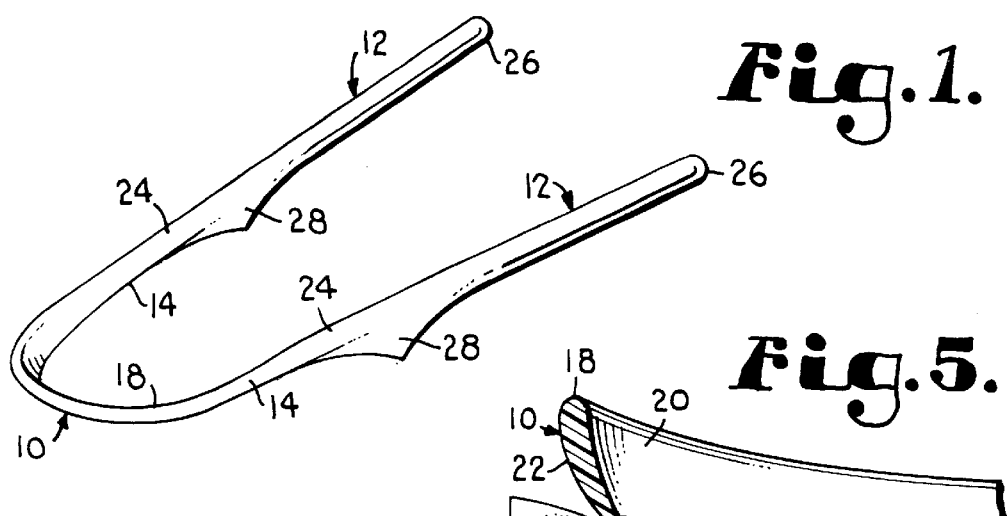
*Fig.1.*
*Fig.5.*
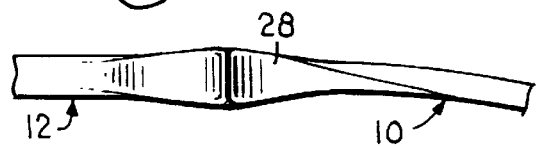
*Fig.4.*
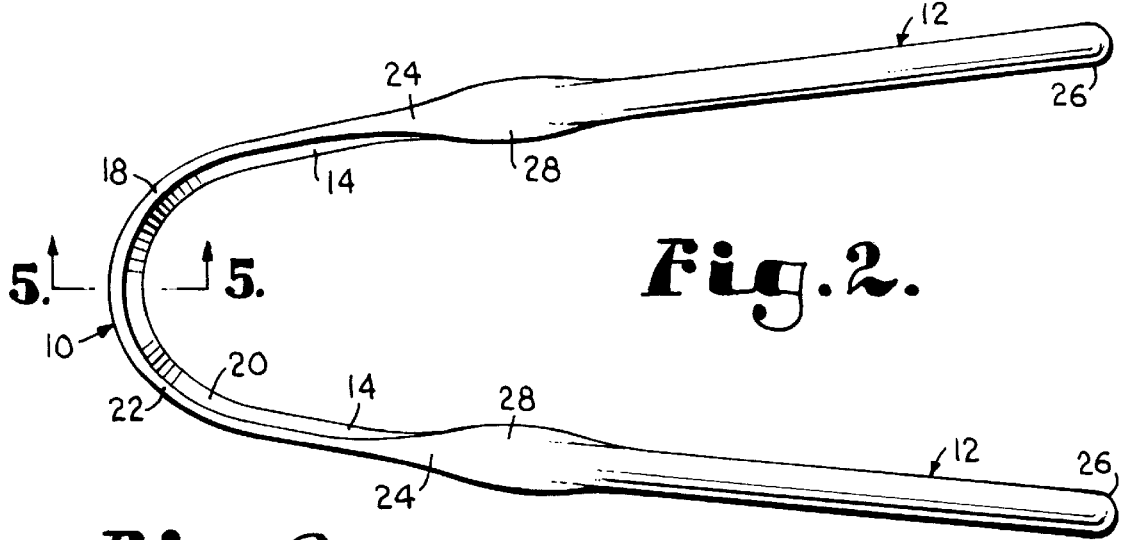
*Fig.2.*
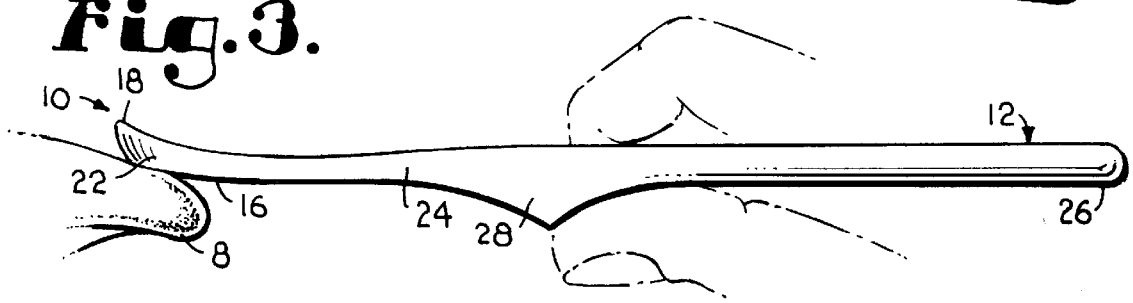
*Fig.3.*

TONGUE SCRAPING APPARATUS

BACKGROUND OF THE INVENTION

The present invention relates generally to instruments for use by humans in cleaning their tongues, and more particularly to a tongue scraping apparatus that can be used to clean the tongue and reduce plaque and mouth odor.

It is known that plaque collects on the tongue as well as on the teeth of humans, and that this collection of bacteria and other microorganisms is the primary source of halitosis. It has long been known that frequent tooth brushing reduces the build-up of plaque on the teeth. However, such brushing does not effectively remove plaque from the tongue, even when a conventional brush is used on the tongue during every tooth brushing.

More recently, instruments have been developed for scraping the upper surface of the tongue to remove plaque more completely than is possible with a brush. These instruments take one of several forms. For example, it is known to provide a flat strip of synthetic resin material that is flexible to permit the strip to be bent into a U-shaped blade that can be drawn outward over the tongue to dislodge plaque from the tissue of the tongue. An alternate design includes a curved blade having a generally rectangular cross-sectional shape presenting opposed upper and lower scraping edges, and a pair of proximal ends that are connected to handles by which the instrument can be gripped. Yet another type of known tongue scraping instrument includes a single elongated handle that is attached to a spoon-shaped blade that is drawn outward over the tongue to remove plaque from the tongue tissue.

Although the principle behind each of these known constructions is to scrape plaque from the upper surface of the tongue, various drawbacks exist that render the instruments either unsanitary or difficult and troublesome to use.

SUMMARY OF THE INVENTION

It is an object of the present invention to provide a tongue scraping apparatus that is biomechanically engineered for safety, convenience and hygiene, including a physiologically contoured blade, and a pair of handles that support the blade up off of a support surface when not in use.

It is another object of the invention to provide such an apparatus with a blade having only a single cleaning edge, wherein the opposing edge is smooth to prevent the blade from abrading the delicate tissue in the roof of the user's mouth during tongue cleaning.

In accordance with these and other objects evident from the following description of a preferred embodiment of the invention, a tongue scraping apparatus is provided for use in cleaning the upper surface of a user's tongue, wherein the apparatus includes a curved blade presenting a parabolic plan shape, and a pair of handles by which the apparatus may be gripped. The blade includes a relatively sharp lower edge, an opposed, relatively smooth upper edge, opposed front and back arcuate faces extending between and connecting the lower and upper edges together, and a pair of proximal ends to which the distal ends of the handles are connected. The handles each include a proximal free end opposite the distal end, and a depending thumb press adjacent the distal end for facilitating gripping of the handles.

The center of gravity of the apparatus is preferably offset from the thumb presses of the handles in a direction toward the free ends of the handles such that the apparatus rests on the free ends of the handles and the thumb presses when placed on a horizontal support surface. In addition, the blade presents an arcuate horizontal profile so that the lower edge of the blade possesses a high-centered contour matching that of a tongue.

By providing an apparatus in accordance with the present invention, numerous advantages are realized. For example, by employing a blade having a relatively sharp lower edge and a smooth upper edge, it is possible to draw the blade outward over the tongue during cleaning without running the risk of abrading or cutting tissue in the roof of the mouth with the upper edge of the blade. In addition, the handles are weighted and contoured to facilitate handling of the apparatus and to support the blade up off of a support surface when not in use.

BRIEF DESCRIPTION OF THE DRAWING

The preferred embodiment of the present invention is described in detail below with reference to the attached drawing figures, wherein:

FIG. 1 is a perspective view of a tongue scraping apparatus constructed in accordance with the preferred embodiment;

FIG. 2 is a top plan view of the apparatus;

FIG. 3 is a side elevation view of the apparatus;

FIG. 4 is a fragmentary bottom plan view of the apparatus; and

FIG. 5 is a sectional view taken along line 5—5 of FIG. 2.

DETAILED DESCRIPTION OF THE PREFERRED EMBODIMENT

A tongue scraping apparatus constructed in accordance with the preferred embodiment is illustrated in FIG. 1, and broadly includes a blade 10 and a pair of handles 12. The blade and handles are preferably formed as a unitary piece of shape-retaining synthetic resin material, e.g. by an injection molding process or the like, but may be formed as separate elements that are connected together by an adhesive or other suitable fastening expedient.

The blade 10 is curved, presenting a parabolic plan shape having an apex defining the distal tip of the apparatus, and a pair of opposed proximal ends 14. As shown in FIG. 5, the blade includes a relatively sharp lower edge 16, an opposed, relatively smooth upper edge 18, and opposed front and back faces 20, 22 extending between and connecting the lower and upper edges together. The lower edge 16 is the cleaning edge that is drawn across the tongue 8 during cleaning. The upper edge of the blade does not serve a purpose during cleaning, but is shaped with a smooth edge to prevent the blade from abrading or cutting the delicate tissue in the roof of the user's mouth during cleaning. Accordingly, the resulting blade design is safe and easy to use, and does not present a risk to the surrounding oral tissues. The front face 20 of the blade defines the attack angle of the blade to the tongue, and is preferably of a concave shape that channels lifted material from the tongue along the length of the blade.

As shown in FIG. 3, the blade 10 has an arcuate horizontal profile that is upturned at the distal end such that the lower edge 16 of the blade possesses a high-centered contour matching the physiological shape of a tongue. In other words, the three-dimensional shape of the lower edge of the blade is much the same as that naturally assumed by a flaccid piece of thread or the like that is placed on the posterior of the tongue and drawn downward and outward from the mouth. By providing this construction of the blade 10, a generally uniform pressure is applied by the blade across the tongue, facilitating thorough plaque removal.

Preferably, the blade is formed of a material that permits the proximal ends of the blade to be pulled apart from one another to adjust the width of the apparatus to accommodate mouths of various sizes. As such it is not necessary to construct the apparatus in different sizes.

As illustrated in FIG. 2, the handles 12 are elongated, each including a pair of opposed axial ends 24, 26 and a depending thumb press 28. As shown in FIG. 4, the thumb press of each handle is located adjacent the distal end 24 thereof adjacent the blade, and facilitates gripping of the apparatus. The handles 12 are preferably formed thicker or of a greater diameter than the blade to improve handling of the apparatus, and the center of gravity of the apparatus is offset from the thumb presses 28 in a direction toward the free ends 26 of the handles such that the apparatus rests on the proximal ends of the handles and the thumb presses when placed on a horizontal support surface.

With reference again to FIG. 2, the distal end 24 of each handle 12 presents a convex, preferably rounded surface adjacent the front face 20 at the ends 14, of the blade 10. As mentioned, the front face of the blade is concave to channel liquids away from the tongue during use. However, by shaping the handles 12 with a convex surface abutting the ends of the blade, liquid is collected on the front face 20 of the blade and is inhibited from dripping down the handles onto the hands of the user.

During use, as shown in FIG. 3, the apparatus is gripped by the handles 12, with the thumbs of the user placed against the thumb presses 28 and is lifted to the mouth of the user and positioned with the blade in the back of the mouth over the tongue. The thumb presses 28 provide a convenient indexing reference to prevent the blade from being positioned too far into the mouth where it might cause gagging of the user. Scraping is achieved by lowering the cleaning edge 16 of the blade onto the tongue and pulling downward and outward on the handles 12 with a force sufficient to dislodge plaque from the tissue of the tongue. The plaque is lifted onto the front face 20 of the blade, as shown in FIG. 5, and channeled away from the tongue to permit scraping of the entire length of the tongue in a single stroke, while the handles prevent the plaque from dripping onto the hands of the user. Because the thumb presses 28 facilitate application of uniform pressure on the tongue, it is less likely that a gag reflex will be triggered during scraping.

If it is necessary to put the apparatus down, either during or between uses, it can be placed right-side-up on a support surface so that the handles support the apparatus with the blade up out of contact with the surface. As such, a convenient and hygienic design results which is safe to put down on a sink or other support surface containing bacterial contamination without the risk of contaminating the blade.

The construction of the preferred embodiment is safe, hygienic and convenient, as well as being simple and comfortable to use. It is designed with a single cleaning edge so as to reduce the possibility of damage to surrounding oral tissue during use, and the edge is capable of removing plaque from the tongue in a single stroke due to the physiological contour thereof. The flexibility of the material used in the apparatus permits the blade to be flexed to accommodate tongues of various sizes, and to permit the user to manipulate the apparatus to view the blade during cleaning. If desired, an antibacterial material could be combined with the synthetic resin of the apparatus to prohibit the growth of bacteria on the apparatus during the useful life thereof. Alternately, the apparatus could be constructed as a single or multiple use device.

Although the present invention has been described with reference to the preferred embodiment, it is noted that equivalents may be employed and substitutions made herein without departing from the scope of the invention as recited in the claims.

What is claimed is:

1. A tongue scraping apparatus for use in cleaning the upper surface of a user's tongue, the apparatus comprising:

a curved blade presenting a parabolic plan shape and including a relatively sharp lower edge, an opposed, relatively smooth upper edge, opposed front and back faces extending between and connecting the lower and upper edges together, and a pair of proximal ends; and a pair of elongated handles, each including a distal end connected to one of the proximal ends of the blade, a proximal free end, and a depending thumb press adjacent the distal end of the handle for facilitating gripping of the apparatus, wherein the center of gravity of the apparatus is offset from the thumb presses in a direction toward the proximal ends of the handles such that the apparatus rests on the proximal ends of the handles and the thumb presses when placed on a horizontal support surface.

2. An apparatus as recited in claim 1, wherein the blade is formed of a material that permits the proximal ends of the blade to be pulled apart from one another to adjust the width of the apparatus.

3. An apparatus as recited in claim 1, wherein the blade and handles are formed of a synthetic resin material that retains the parabolic shape of the blade while permitting the proximal ends of the blade to be pulled apart from one another to adjust the width of the apparatus.

4. An apparatus as recited in claim 1, wherein the apparatus is formed of an antibacterial material.

5. A tongue scraping apparatus for use in cleaning the upper surface of a user's tongue, the apparatus comprising:

a curved blade presenting a parabolic plan shape and including a relatively sharp lower edge, an opposed, relatively smooth upper edge, opposed front and back faces extending between and connecting the lower and upper edges together, and a pair of proximal ends; and a pair of elongated handles, each including a distal end connected to one of the proximal ends of the blade, a proximal free end, and a depending thumb press adjacent the distal end of the handle for facilitating gripping of the apparatus, wherein the blade presents an arcuate horizontal profile so that the lower edge of the blade possesses a high-centered contour matching the physiological shape of a tongue.

6. An apparatus as recited in claim 5, wherein the blade is formed of a material that permits the proximal ends of the blade to be pulled apart from one another to adjust the width of the apparatus.

7. An apparatus as recited in claim 5, wherein the blade and handles are formed of a synthetic resin material that retains the parabolic shape of the blade while permitting the proximal ends of the blade to be pulled apart from one another to adjust the width of the apparatus.

8. An apparatus as recited in claim 5, wherein the apparatus is formed of an antibacterial material.

9. A tongue scraping apparatus for use in cleaning the upper surface of a user's tongue, the apparatus comprising:

a curved blade presenting a parabolic plan shape and including a relatively sharp lower edge, an opposed, relatively smooth upper edge, opposed front and back faces extending between and connecting the lower and upper edges together, and a pair of proximal ends; and a pair of elongated handles, each including a distal end connected to one of the proximal ends of the blade, a proximal free end, and a depending thumb press adjacent the distal end of the handle for facilitating gripping of the apparatus, wherein the front face of the blade is concave to channel liquids away from the tongue during use, and the distal ends of the handles are convex to prevent the liquids from dripping onto the handles.

10. An apparatus as recited in claim 9, wherein the blade is formed of a material that permits the proximal ends of the blade to be pulled apart from one another to adjust the width of the apparatus.

11. An apparatus as recited in claim 9, wherein the blade and handles are formed of a synthetic resin material that retains the parabolic shape of the blade while permitting the proximal ends of the blade to be pulled apart from one another to adjust the width of the apparatus.

12. An apparatus as recited in claim 9, wherein the apparatus is formed of an antibacterial material.

13. A tongue scraping apparatus for use in cleaning the upper surface of a user's tongue, the apparatus comprising:

a curved comprising presenting a parabolic plan shape and including a pair of proximal ends; and a pair of enlongated handles, each including a distal end connected to one of the proximal ends of the blade, a proximal free end, and a depending thumb press adjacent the distal end of the handle for facilitating gripping of the apparatus, the center of gravity of the apparatus being offset from the thumb presses in a direction toward the proximal ends of the handles so that the apparatus rests on the proximal ends of the handles and the thumb presses when placed on a horizontal support surface.

* * * * *